(12) United States Patent
Sanz et al.

(10) Patent No.: US 8,637,439 B2
(45) Date of Patent: Jan. 28, 2014

(54) BATHING GEL WITH IMPROVED ENVIRONMENTAL PROFILE

(75) Inventors: Eva Vinas Sanz, Barcelona (ES); Marta Queralt Lopez Salvans, Manresa (ES)

(73) Assignee: Coty Inc., New York, NY (US)

( * ) Notice: Subject to any disclaimer, the term of this patent is extended or adjusted under 35 U.S.C. 154(b) by 0 days.

(21) Appl. No.: 13/519,550

(22) PCT Filed: Dec. 16, 2010

(86) PCT No.: PCT/US2010/003187
§ 371 (c)(1),
(2), (4) Date: Sep. 14, 2012

(87) PCT Pub. No.: WO2011/090465
PCT Pub. Date: Jul. 28, 2011

(65) Prior Publication Data
US 2013/0005634 A1    Jan. 3, 2013

(30) Foreign Application Priority Data
Dec. 28, 2009   (ES) .................................. P200931282

(51) Int. Cl.
*A61K 8/00*    (2006.01)
(52) U.S. Cl.
USPC ............................ 510/130; 510/135; 510/159
(58) Field of Classification Search
None
See application file for complete search history.

(56) References Cited

U.S. PATENT DOCUMENTS 6,033,680 A    3/2000  Dixon et al.
6,191,083 B1 *  2/2001  Brooks et al. ................. 510/124

FOREIGN PATENT DOCUMENTS

| EP | 0878189 A2 | 11/1998 |
|---|---|---|
| WO | WO-9114759 A1 | 10/1991 |
| WO | WO-9501152 A1 | 2/1995 |
| WO | WO-2011090465 A2 | 7/2011 |
| WO | WO-2011090465 A3 | 7/2011 |

OTHER PUBLICATIONS

"International Application U.S. Appl. No. PCT/US2010/003187, International Search Report mailed Aug. 11, 2011", 4 pgs.
"International Application U.S. Appl. No. PCT/US2010/003187, Written Opinion mailed Aug. 11, 2011", 9 pgs.
"Spanish Patent Application No. 200931282; Office Action Response Filed: Sep. 16, 2010", 69 pgs.
"Spanish Patent Application No. 200931282; Office Action Response Filed: Nov. 19, 2010", 2.
"International Application U.S. Appl. No. PCT/US2010/003187, International Preliminary Report on Patentability mailed Jul. 12, 2012", 10 pgs.

* cited by examiner

*Primary Examiner* — Necholus Ogden, Jr.
(74) *Attorney, Agent, or Firm* — Schwegman Lundberg & Woessner, P.A.

(57) ABSTRACT

Compositions adapted for use as a bathing (shower or bath) gel for personal cleansing are provided, the compositions containing reduced loadings of relatively harsh anionic surfactants and of fragrance oils, but retaining a spectrum of functional properties perceived by consumers as desirable. The compositions include lower concentrations of anionic surfactants compared to standard bathing gel compositions, but the addition of quantities of a long-chain alkyl, hydroxyalkyl cellulose derivative to the composition preserves or enhances functional properties such as viscosity, skin mildness, foam generation on lathering, subjective perceived cleansing appreciation, and fragrance performance. The bathing gels provide an environmental benefit such as reduced surfactant loading, biodegradability, and aquatic toxicity of wastewater streams when used in the place of standard bathing gels.

34 Claims, 9 Drawing Sheets

BATHING GEL WITH IMPROVED ENVIRONMENTAL PROFILE

CROSS-REFERENCE TO RELATED APPLICATION

This application is a U.S. National Stage Filing under 35 U.S.C. 371 of International Patent Application Serial No. PCT/US2010/003187, filed Dec. 16, 2010, and published on Jul. 28, 2011 as WO 2011/090465, which claims the priority of Spanish Patent Application Serial No. P200931282, filed Dec. 28, 2009, which are both incorporated herein by reference in their entirety.

BACKGROUND

Personal cleansing products such as soaps and detergents are used by people worldwide, resulting in an aggregate daily release of vast quantities of these materials in wastewater streams into the environment. Among products used for personal cleansing, classical soaps, i.e. the salts of fatty acids, are no longer the preferred compositions for a variety of reasons. For example, soaps are perceived to be relatively harsh or irritating to skin and eyes, are not easy to formulate in consumer-preferred formulations such as gels, do not foam well or leave skin feeling clean after use particularly when the water used in personal cleansing contains impurities such as ions, and are not particularly good vehicles for delivery of benefit agents such as fragrances. Soaps are prone to perform particularly badly in hard water, forming insoluble precipitates with ions such as Ca, Mg, Mn, and Fe that greatly interfere with cleansing.

Many compositions have been developed based on chemical substances other than classical soaps, and most include surfactants of various types, also known as syndets, that serve to solubilize oils, greases, and other soiling substances, allowing them to be washed off skin in a shower or bath. Personal cleansing compositions that are composed of surfactants other than salts of fatty acids, that provide for good foam generation, improve the perception by the user of benefit agents such as fragrances, are mild to skin, and provide a positive perception of cleansing performance, are widely used.

However, many if not all such commercial personal cleansing products contain surfactants such as anionic surfactants that can be relatively harmful to aquatic organisms especially at high concentrations and are a significant component of wastewater streams effluxed by residential units worldwide. Some of these surfactants have poor biodegradability and are thus persistent in the environment. Fragrance compounds (usually chemical mixtures, also termed fragrance oils) are another example of a component of many personal cleansing products that can be of low biodegradability and can exert a toxic effect on aquatic organisms exposed to wastewater containing residues of the fragrance compounds. The presence of these components in personal cleansing products available on the commercial market results in discharge of treated or untreated wastewater effluent containing at least some of the components into streams, rivers, oceans, and groundwater, sometimes with detrimental results.

The presence of surfactants such as anionic surfactants, and fragrance oils, in the discharged treated wastewater can be harmful to aquatic organisms in the receiving waters. The effect is more pronounced at higher concentrations of the contaminants in the wastewater. The types of organisms that can be damaged include beneficial microorganisms, invertebrate and vertebrate animals, beneficial algae, and higher plants. Also, when fresh water into which such wastewater streams are taken up for use as drinking water, the presence of such contaminants can complicate the efforts required to produce potable water for human use. See, for example the document entitled "Environmental and Health Assessment of Substances in Household Detergents and Cosmetic Detergent Products," Torben Madsen et al., Danish Environmental Protection Agency, Centre for Integrated Environment and Toxicology (CETOX), Environmental Project No. 615, 2001, at http://www2.mst.dk/udgiv/Publications/2001/87-7944-596-9/pdV87-7944-597-7.pdf.

Aquatic toxicity and challenges to water purity are of increasing concern due to the worldwide population growth of the human population and increased per capita consumption by many individuals. Many indicator species, such as amphibians like frogs and salamanders, have exhibited alarming decreases in their populations over the last several decades. The sensitive skins of such animals may be particularly sensitive to the impact of surfactants present in their watery habitats that arise from human use. Surfactants are also know to cause problems for waterfowl, stripping the natural feather oils from the birds and rendering them prone to hypothermia. When feathers become wet due to stripping of the natural protective skin oils by surfactants, such birds are also impaired in their ability to fly. Due to the impact of surfactants on cell membranes, various aquatic invertebrates are also at risk from surfactant contamination. Oyster populations have been impacted through the discharge of surface-active synthetic compounds into marine littoral environments from sewage treatment facilities. Populations of less visible species, such as insect larvae and single-celled animals, are likely also damaged by the presence of surfactants.

Nevertheless, surfactants are extremely valuable to the human population for various washing and cleansing purposes. Frequent personal bathing and washing of hands, etc., is vital to maintaining public health, reducing the spread of pathological organisms and preventing epidemics. In general, humans appreciate being clean and appreciate cleanliness in others. Consequently, use of compositions containing surfactants is likely to continue. Therefore, it is desirable to devise cleansing compositions for personal use in bathing that are acceptable to consumers, yet reduce their impact on the environment when discharged in wastewater effluents such as bath water. By mitigating human impact on the ecosystems in which humans live, environmental sustainability of human populations can be improved without loss of any valuable and appreciated quality of life.

SUMMARY

The present invention is directed to compositions adapted for use as bathing (shower or bath) compositions, typically referred to as bath or shower gels, in personal cleansing. The compositions of the present invention provide comparable or superior cleansing attributes from the perspective of the user while at the same time providing a benefit to an ecosystem and to the environment as a whole. Use of the inventive compositions as a substitute for the use of standard personal cleansing compositions presently on the market can result in generation of cleaner wastewater effluents with an improved environmental profile.

As discussed above, many personal cleansing products on the world markets today have components such as surfactants and fragrance oils that can be persistent in wastewater streams and in the environment, and having a certain degree of toxicity to aquatic organisms they can be harmful to an ecosystem into which they are discharged. Long term, large scale use of such personal cleansing products can have a deleterious effect on a wide variety of organisms that share the planet Earth with human beings. Use of compounds of the invention can provide equal or superior cleansing performance to the consumer and at the same time have a reduced deleterious impact on the environment resulting from the discharge of surfactants and fragrance compounds into wastewater.

In various embodiments, the present invention provides compositions and methods that enable consumers to use a product for personal cleansing that enable the consumers to reduce their negative impact on wastewater streams and thus on water pollution and harm to aquatic organisms worldwide. The compositions of the invention have many of the desirable attributes of personal cleansing products that the consumers now use and are familiar with, and provide at least equal cleansing appreciation, foaming, fragrance performance, and the like. By incorporating a naturally-derived component into the inventive compositions, a derivative of natural cellulose, a composition can be obtained that can contain reduced amounts of potentially harmful surfactants and fragrance oils relative to standard personal cleansing products now on the market, while maintaining the performance attributes that consumers have come to expect. Use of an inventive composition as a substitute for presently available personal cleansing compositions can reduce negative impacts on the environment while retaining properties that consumers value in personal cleansing products.

In various embodiments, the invention provides a composition for use as a bathing gel personal cleansing product by human users, comprising:
(a) no more than about 11.5% w/w of an anionic surfactant;
(b) no more than about 3% w/w of a zwitterionic surfactant;
(c) no less than about 0.1% w/w of a long-chain alkyl hydroxyalkyl cellulose; and
(d) water,
and optionally further comprising up to no more than about 2% w/w of a non-ionic surfactant, or up to no more than about 3% w/w of a fragrance oil, or both.

In various embodiments, an inventive composition can be in the form of a viscous liquid or a gel, adapted for use in bathing, that performs its cleansing functions at least as well as present commercial personal cleansing products, but contains lower percentages of potentially harmful surfactants and of fragrance oils.

In various embodiments, the inventive composition can deliver the same perceived performance to the user in terms of parameters such as viscosity, foam generation and longevity, fragrance intensity and persistence, skin mildness, and user cleansing appreciation, as do commercial cleansing products having higher concentrations of surfactants, fragrance oils, or both, but lacking the long-chain alkyl hydroxyalkyl cellulose.

In various embodiment, the invention provides a composition wherein a fragrance oil is present at a lower concentration than a fragrance oil of a comparable composition lacking the long-chain alkyl hydroxyalkyl cellulose derivative and having a higher content of the anionic surfactant, wherein fragrance performance on skin, fragrance performance in container headspace, or both, is no less than that of the comparable composition.

In various embodiments, the inventive composition provides a lesser degree of aquatic toxicity and a greater degree of biodegradability in wastewater streams when used in a comparable amount to a commercially available personal cleansing product such as a shower or bath gel.

In various embodiments, the invention provides a use of the composition of the invention for preparation of a personal cleansing product.

In various embodiments, the invention provides a method of reducing a surfactant concentration in bath or shower wastewater, comprising use by a person for personal cleansing in the bath or shower of a quantity of the composition of the invention as a substitute for use of a comparable quantity of a comparable composition lacking the long-chain alkyl hydroxyalkyl cellulose derivative and having a higher content of the anionic surfactant.

In various embodiments, the invention provides a method of decreasing a surfactant load on a wastewater treatment facility, comprising use by a person for personal cleansing in the bath or shower of a quantity of the composition of the invention as a substitute for use of a comparable quantity of a comparable composition lacking the long-chain alkyl hydroxyalkyl cellulose derivative and having a higher content of the anionic surfactant In various embodiments, the invention provides a method of reducing toxicity of wastewater to organisms in contact with the wastewater caused by use of a quantity of a shower gel or bath gel personal cleansing product, comprising use by a person for personal cleansing in the bath or shower of the equivalent quantity of a composition of the invention.

In various embodiments, the invention provides a method of improving biodegradability of wastewater resulting from use of a shower gel or bath gel personal cleansing product, comprising use by a person for personal cleansing in the bath or shower of the equivalent quantity of a composition of the invention.

In various embodiments, the invention provides a method of reducing the amount of fragrance oil discharge by wastewater into an ecosystem resulting from use of a quantity of a shower gel or bath gel personal cleansing product, comprising use by a person for personal cleansing in the bath or shower of the equivalent quantity of a composition of the invention.

In various embodiments, the invention provides a method of improving environmental sustainability resulting from use of a shower gel or bath gel personal cleansing product, comprising use by a person for personal cleansing in the bath or shower of the equivalent quantity of a composition of the invention.

DETAILED DESCRIPTION

Figure 1:
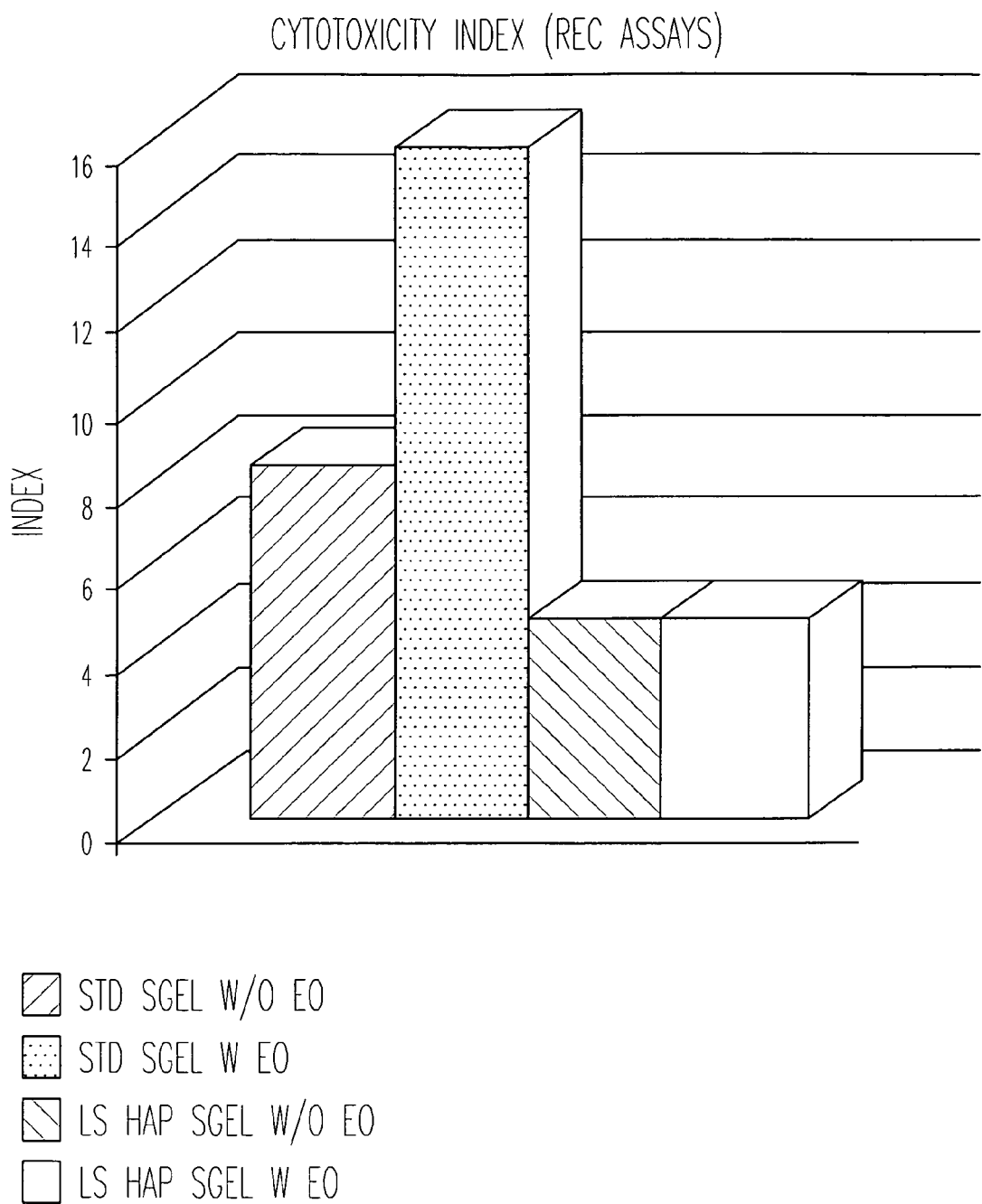
FIG. 1 is a bar graph depiction of the relative cytotoxicity as measured by the REC method of a bathing gel composition compared to a standard bathing gel composition.

As the term is used herein, a "personal cleansing product" refers to a composition such as a bath or shower gel or liquid ("bathing gel") that is used by human beings in conjunction with water for bathing, i.e., washing their bodies and parts thereof, such as on a routine or daily basis. "Bathing" as the term is used herein includes personal ablutions performed in a bath or hot tub or other body of water, and includes showering performed in conjunction with use of a stream or spray of water, and also includes "sponge baths" using water absorbed in cloth or other absorbent material. Localized washing such as hand and face washing and localized cleansing of any other external body regions is included in the term as used herein.

A "bathing gel" refers to a personal cleansing product that is a viscous liquid or gel, suitable for dispensing from consumer packaging such as a plastic or glass bottle or other container, that is applied to skin and mixed with water to produce a cleansing foam when bathing as defined above, the foam then being washed off to remove oils, greases, dirt, and soils of various types. A "gel" within the meaning herein can be flowable, such that it can be dispensed from a squeeze bottle using hand pressure, and includes a liquid of a viscosity substantially greater than the viscosity of water.

The personal cleansing product of the invention can be but need not be packaged in a bottle or multi-unit container; packaging for consumer use in envelopes, bags, tubes, squeeze dispensers, piston-type dispensers and other consumer packaging forms is also included. In various embodiments, the bathing gel can be dispensed by any means employed for dispensing flowable compositions for bathing purposes. The cleansing product herein can also be used for washing by others of children or elderly people unable to carry out their own personal washing, or for washing of pets such as dogs or horses.

A "composition" as the term is used herein, referring to a composition of the present invention or a control composition, refers to the mixture as specified including water, as it would be packaged for use and used in bathing by the consumer. Accordingly, when a "quantity" of a composition is referred to herein, the reference is to an amount, by weight or volume, of the composition as it would be used by the human, including the water diluting the active ingredients. Thus a "quantity" of an inventive composition that contains a lower "content" or "percentage" of an anionic surfactant than does an equivalent "quantity" of a control composition in fact contains a lesser absolute amount of the anionic surfactant although the quantities of the compositions are equivalent.

A "standard composition" or "control composition" as the terms are used herein is a bathing gel composition used for comparison with a composition of the invention with respect to various properties and parameters. A standard or control composition is analogous to an embodiment of a composition of the invention except that it contains a relatively high concentration or content of an anionic surfactant or a mixture of anionic surfactants and fragrance oils, and it lacks the long-chain alkyl hydroxyalkyl cellulose derivative component.

A "surfactant," as is well known in the art, is a chemical composition, a molecular entity that possesses the property of reducing interfacial surface tension between water and water-insoluble substances such as oils or greases. A surfactant can also be effective in suspending solid materials, such as dirt particles, in water. Such substances are also known as "amphiphilic materials," the molecules making up bulk quantities possessing both hydrophilic and lipophilic moieties, that serve to interact with water and water-immiscible substances at the interface.

An "anionic surfactant" as used herein refers to a surfactant that contains one or more molecular moieties that bear a net negative electrical charge. An anionic surfactant can contain a group such as a sulfate or a phosphate or a carboxylate in an ionic form, i.e., that exists in ionic form in water solution at neutral or near-neutral pH. An anionic surfactant also contains a hydrophobic group that is covalently bonded to the moiety that bears the negative charge. Thus, an anionic surfactant within the meaning herein includes long chain alkyl sulfates, sulfonates, carboxylates, and the like. An example is sodium dodecylsulfate. Another example is sodium laureth sulfate, i.e., sulfated hydroxyethylated dodecanol. A further example is an alkyl sarcosinate (N-(long-chain alkanoyl),N-methylglycinate salt). In the context of surfactants, anionic surfactants can be referred to as "anionics."

A "zwitterionic surfactant" as used herein refers to a surfactant wherein the molecular entity contains both a positive and a negative electrical charge comprised by molecular moieties that are covalently bonded to a lipophilic moiety. Various zwitterionic surfactants contain a "betaine" group, i.e., a group containing a carboxylate group (anionic) and a quaternary ammonium group (cationic). An example is cocamidopropylbetaine, i.e., a fatty amide bonded via a propyl group to a N,N-dimethylglycinate moiety such that the glycine nitrogen atom is quaternary (cationic), A "nonionic surfactant" is a surfactant that does not contain a group that is ionized at neutral or near-neutral pH in water, but is nevertheless amphipathic, containing both lipophilic and hydrophilic moieties. Examples are fatty esters of sugars such as glucose, wherein the sugar hydroxyl groups make up the hydrophilic moiety.

"Fragrance oils" or "fragrance compounds" are typically a complex mixture of multiple molecular components, usually liquid at room temperature, although some of the individual raw materials could be solid at room temperature, that provide a desirable or attractive odor to a composition, such as are well known in the art. Such materials are also referred to as "fragrances," 'perfumes," "essential oils," "EO," and the like. These materials consist of a combination of ingredients having pleasing organoleptic properties as perceived by humans and comprise single materials, complex reaction mixtures and natural, basically botanical, derived compounds. Examples include various organic molecules such us octadienes, hexyloxyacetonitriles, cyclopentane derivatives, aliphatic dibasic acid diesters, 3-(10-undecenyloxy)propionitrile, tricyclodecane-methylol derivatives, 2-methyl-2-alkyl-alkanoic esters, tri-methylcyclonexylethyl ethers, cyanoethylidenebicycloheptenes, crotonyltrimethyl cy-clohexanes, nonanols, nonenols, α-oxo mercaptanes, safranic acid esters and maltyl-2-methyl alkenoates (see, for example, Goronszy, M. C. (1992), Treatment of perfume manufacturing wastewaters by co-metabolism with an alcohol substrate, Water Science & Technology 25 (3), 131-141). Examples include lavender oil, rose oil, lilac essence, lily-of-the-valley essence, and the like.

A "long-chain alkyl" group or derivative refers to a lipophilic moiety or substance that at the molecular level includes long chain, i.e., more than about 10 carbon atoms, hydrocarbon chains, such as n-dodecyl, n-hexadecyl, and the like. A long-chain alkyl group within the meaning herein can include a mixture of different long-chain alkyl forms, such as are commonly obtained from natural sources or from separation processes.

Examples of long-chain alkyl include cetyl, i.e., hexadecyl, and lauryl, i.e., dodecyl. The chain can be fully saturated or can contain one or more double bonds ("unsaturations"), and although often linear, can include branching groups such as alkyl groups.

A "long-chain alkanoyl" group is a long chain alkyl group bearing a carbonyl group at one terminus through which the group is bonded to another group. An example is a cocoyl group, which is an alkanoyl group include a mixture of various long chain alkyl groups. An unsaturated example is oleoyl, octadec-9-enoyl.

"Cellulose," as is well known in the art, refers to poly-β(1, 4)-D-glucose, typically obtained from wood pulp, cotton, or other plant sources. There are also celluloses derived from bacteria. A "hydroxyalkyl cellulose" is a cellulosic polymer that results from the reaction of cellulose or a derivative thereof with an epoxide, such as ethylene oxide (hydroxyethyl cellulose) or propylene oxide (hydroxypropyl cellulose). A "long-chain alkyl hydroxyalkyl cellulose" within the meaning herein refers to a substance composed of molecules of cellulose that are covalently bonded to both hydroxyalkyl groups and long-chain alkyl groups. An example is cetyl hydroxyethyl cellulose, i.e., hydroxyethylated cellulose that has been reacted with cetyl alcohol (1-hexadecanol). A long-chain alkyl hydroxyalkylcellulose is thus a polymeric material containing both hydrophilic and lipophilic domains therein.

"Viscosity" refers to the thickness or resistance to flow of a liquid or gel composition, as is well known in the art.

"Skin mildness" refers to the propensity of a solution of a cleansing product to avoid irritation or inflammation of living human skin. A cytotoxicity index can be used to gauge skin mildness in that substances benign to skin can have low cytotoxicity.

"Foam generation" refers to the volume, density, and the longevity or persistence of a lather produced by agitating a solution of the cleansing product in water, such as by rubbing it against skin with a hand or between hands.

"Cleansing appreciation" refers to a subjective judgment by a user of the composition under bath or shower conditions as to how clean the skin or body feels to the user following use and rinsing from the skin.

"Fragrance performance on skin" refers to an intensity of the odor as perceived by the user of a fragrance residue left on living human skin following use of the composition under bath or shower conditions.

"Fragrance performance in container headspace" refers to an intensity of odor as perceived by the user of a fragrance in the headspace of a bottle or other container used to hold the composition prior to use, i.e., after opening the container but before using the composition.

"Wastewater" refers to the water from the bath or shower that contains residues of the personal cleansing products used by a person therein, or to the combined residential sewage effluent produced by one or more residential units wherein people are bathing or showering, or to the effluent from a sewage treatment facility that receives, among other wastestreams, effluent from the residential units or other sources containing the effluent from personal cleansing.

"Toxicity to organisms" refers to acute or chronic toxicity of a water solution containing some percentage of a composition, such as an inventive composition or a comparison composition, to organisms that normally spend all or part of their existence immersed in or in contact with a water habitat. Such organisms include microorganisms, invertebrate animals, and vertebrate animals, that spend all or part of their life cycle in or near water, or ingest the water; and plants, both unicellular and multicellular, that come in contact with water containing the composition, such as ground water. Examples of microorganisms include bacteria and protozoans; examples of invertebrate animals include insects such as juvenile stages and other multicellular water-dwelling organisms; vertebrate animals include fish, amphibians, and reptiles that reside in the water, and reptiles, birds, and mammals that either swim in, or drink, the water in question. Examples of plants include algae and purely aquatic plants, including seaweeds, that live in the water, and land plants that are exposed to the water through groundwater contact, irrigation, and the like. Anionic surfactants, such as sulfate-based surfactants, among others, are known to act detrimentally at some concentrations on living organisms such as by interference with the normal functioning of cell membranes and the like.

"Biodegradation" refers to the breakdown of chemical components of a composition in the natural environment, such as in an aquatic ecosystem into which wastewater containing sewage effluent is discharged, by natural factors such as bacterial, fungal, or photochemical mechanisms and the like. Within the meaning herein, a chemical component need not be converted to carbon dioxide and water for biodegradation to have occurred, but at least a component having some toxicity must have been converted by a naturally occurring mechanism or process to a compound or compounds of lesser toxicity.

"Decreasing a surfactant load in wastewater" and "reducing a surfactant concentration in wastewater" refer to a decrease or reduction in a concentration of one surfactant, or of a combined set of surfactants, depending upon context, in a wastewater stream, such as sewage effluent from a house or other residential unit, or in treated sewage effluent from a wastewater treatment facility. "Decreasing a fragrance oil load in wastewater" and "reducing a fragrance oil concentration in wastewater" refer to a decrease or reduction in a concentration of one fragrance oil, or of a combined set of fragrance oils, depending upon context in a wastewater stream, such as sewage effluent from a house or other residential unit, or in treated sewage effluent from a wastewater treatment facility. An "effluent stream of treated wastewater" is the effluent from a wastewater treatment facility as discharged into surface waters such as streams, rivers, lakes, and the ocean.

"Improving environmental sustainability" as the term is used herein refers to making improvements such as reduced toxicity, enhanced biodegradability, and increased water purity in the water quality of effluent streams of treated wastewater discharged into the environment, thereby sustaining environmental health in the surrounding ecosystem and reducing the possibly irreversible depletion of biological resources such as aquatic plants, animals, and microorganisms.

In various embodiments the invention is directed to compositions adapted for use as a bathing gel for human use in personal cleansing. The compositions of the invention, while maintaining certain properties valued by consumers and users of cleansing products, also offer environmental benefits compared to other types of personal cleansing products currently on the market. The inventors herein have surprisingly discovered that compositions can be made with reduced concentrations of potentially environmentally detrimental ingredients through the addition of a class of additives prepared from the naturally-produced polymer cellulose, that yet preserve desirable properties such as viscosity, foam generation, cleaning appreciation by users, the performance of benefit agents such as fragrance oils, and skin mildness. The replacement of a portion of potentially environmentally harmful anionic surfactants and fragrance oils by long-chain alkyl hydroxyalkyl cellulose derivatives in bathing gels can provide a personal cleansing product with an improved environmental profile.

In various embodiments the invention provides a composition for use as a bathing gel personal cleansing product by human users, comprising:
(a) no more than about 11.5% w/w of an anionic surfactant;
(b) no more than about 3% w/w of a zwitterionic surfactant;
(c) no less than about 0.1% w/w of a long-chain alkyl hydroxyalkyl cellulose derivative; and
(d) water,
and optionally further comprising up to no more than about 2% w/w of a non-ionic surfactant, or no more than about 3% w/w of a fragrance oil, or both.

In various embodiments, a composition of the invention is in physical state a viscous liquid or a gel at room temperature. Viscosity is influenced by the concentration of surfactant(s) in the composition. Viscosity can also be influenced by the presence of added salt, yet in comparable compositions either lacking in salt or having a definite concentration of salt (e.g, NaCl), various embodiments of the inventive composition are similar in being in physical state of a gel or a viscous liquid, comparable to a composition having a higher total concentration of anionic surfactant(s) and fragrance oils as well as other types of surfactants, yet lacking the long-chain alkyl hydroxyalkyl cellulose derivative.

In various embodiments of the invention, the composition can include no more than about 11.5 w/w, or no more than about 10% w/w, of an anionic surfactant or a mixture of more than one anionic surfactants. More specifically, the composition can include no more than about 9% w/w, or no more than about 8% w/w, or no more than about 7% w/w, of an anionic surfactant or a mixture of more than one anionic surfactants, in combination with no less than about 0.1% of the long-chain alkyl hydroxyalkyl cellulose derivative.

In various embodiments, a composition of the invention can comprise an alketh sulfate, an alkyl sarcosinate salt, or any combination thereof, as an anionic surfactant component. More specifically, an anionic surfactant of an inventive composition can comprise sodium laureth sulfate, sodium lauroyl sarcosate, or sodium cocoyl sarcosate, or any combination thereof.

In various embodiments, a composition of the invention can comprise no more than about 2.4% w/w of the zwitterionic surfactant. For example, a composition can comprise a zwitterionic surfactant component comprising a fatty amidoalkylbetaine, such as cocamidopropylbetaine.

In various embodiments, a composition of the invention can comprise no more than about 0.5% w/w of a non-ionic surfactant. For example, a composition can comprise a non-ionic surfactant comprising a fatty mono-glucoside or a fatty poly-glucoside, or any mixture thereof. More specifically, the fatty glucoside can be coco-glucoside.

In various embodiments, a composition of the invention can comprise no less than about 0.1% w/w, or 0.2% w/w, or 0.3% w/w, or 0.4% w/w, of 0.5% w/w, of the long-chain alkyl hydroxyalkyl cellulose derivative. More specifically, a long-chain alkyl hydroxyalkyl cellulose derivative can comprise cetyl hydroxyethyl cellulose. As is well known in the art, samples of long-chain alkyl hydroxyalkyl cellulose derivatives can have varying molecular weights (weight average and number average), varying degrees of polymerization of the hydroxyethyl component, and varying degrees of substitution of the long-chain alkyl component. More specifically, an example is Natrosol Plus 330 CS®, manufactured by Hercules, Inc.

In various embodiments, a composition of the invention can further comprise additional components well known in the art such as rheological modifiers of either natural or synthetic origin as thickening or suspending agents, e.g., either natural polysaccharides such as xanthan guar, chitosan, guar gum or derivatives thereof, or synthetic polymers, such as acrylate, vinyl, methacrylate, amide polymers or derivatives thereof; conditioner polymers of natural or synthetic origin such as quaternary ammonium salt of acrylamide and dimethyl diallyl ammonium chloride (Polyquaternium-7), quaternary ammonium salt of hydroxyethyl cellulose reacted with a trimethyl ammonium substituted epoxide (Polyquaternium-10), quaternary ammonium derivative of Hydroxypropyl Guar and the like; humectants, i.e., water-binding agents such as polyalcohols like glycerin, propylene glycol and the like; preservatives such as organic acids, e.g., sodium benzoate; anti-oxidants such as tocopherols and their derivatives; and pH adjusters like sodium hydroxide, lactic acid, citric acid and their salts. Other additional components can include vitamins such as vitamin C, D, or E; emollients such as petrolatum, glycerine, and the like; botanical extracts other than fragrances such as Aloe extract (polysaccharides), glycyrrhizin, shea butter, proteins or aminoacids (protein hydrolyzates); sterols such as ruscogenin, sigmasterol and sitosterol; terpenes such as squalene; tannins and lignans (e.g., green tea, bamboo); and the like.

In various embodiments, a composition of the invention can include about 0.5-3.0% w/w of a fragrance oil or a mixture of different fragrance oils, selected to provide a consumer-pleasing organoleptic profile. For example, a composition can comprise no more than about 1.0% w/w, or no more than about 2.0% w/w, or no more than about 3.0% w/w, of a fragrance oil or mixture thereof.

In various embodiments, a composition of the invention can comprise
(a) no more than about 8.0% w/w of an anionic surfactant;
(b) no more than about 2.4% w/w of a zwitterionic surfactant;
(c) no less than about 0.3% w/w of a long-chain alkyl hydroxyalkyl cellulose derivative; and
(d) water;
optionally further comprising up to about 3% w/w of a fragrance oil;
wherein the composition is in physical form a viscous liquid or a gel at room temperature.

For example, a composition can comprise no more than about 0.3% w/w of a non-ionic surfactant, preferably a fatty alkyl glucoside, more preferably coco-glucoside.

In various embodiments, a composition of the invention can comprise a composition wherein a viscosity of the composition is at least as great as a viscosity of a comparable composition lacking the long-chain alkyl hydroxyalkyl cellulose derivative and having a higher content of the anionic surfactant or fragrance oils, or both.

For example, a composition of the invention within the range of weight percentages of ingredients such as is described in Table 1, below, can have a comparable or greater viscosity than a standard shower or bath gel composition such as is shown in Table 2. Various embodiments of the invention can possess a composition within the ranges as shown in Table 1. The total anionic surfactant concentration, a contributor to sample viscosity, is no more than about 8% w/w

TABLE 1

Exemplary Composition of the Invention

| Component | % w/w |
| --- | --- |
| Water | About 85-90 |
| Anionic sulfate-based surfactant | 6.5-8.0 |
| Zwitterionic surfactant | 1.5-3.0 |
| Non-ionic surfactant | 0.15-1.0 |
| Long-chain alkyl hydroxyalkyl cellulose | 0.2-0.5 |
| Fragrance | 0.5-2.5 |
| Other | remainder |

For example, a bathing gel composition of the invention can include about 7% sodium laureth sulfate, about 2.4% cocamidopropylbetaine, about 0.2% coco-glucoside, about 0.3% of cetyl hydroxyethyl cellulose, and about 1% of a fragrance oil.

TABLE 2

Exemplary Control Composition

| Component | % w/w |
| --- | --- |
| Water | About 82-84 |
| Anionic sulfate-based surfactant | 14.2 |
| Zwitterionic surfactant | 1.8 |
| Non-ionic surfactant | 0.8 |
| Long-chain alkyl hydroxyalkyl cellulose | — |
| Fragrance | 0.5-2.5 |
| Other | remainder |

An example of the invention shown in Table 1, including a benefit agent (fragrance oil) and lacking NaCl or other inorganic salt was found to have a viscosity of 55.6 centipoises as measured at 25° C. at speed 100 in a Brookfield spRv3 viscometer. A control composition (also lacking NaCl or other inorganic salt), having a higher anionic surfactant composition but not including a long-chain alkyl hydroxyalkyl cellulose component, such as is shown in Table 2 above, including a benefit agent (fragrance oil) was found to have a viscosity of 17.7 centipoises as measured under the same conditions.

Figure 2:
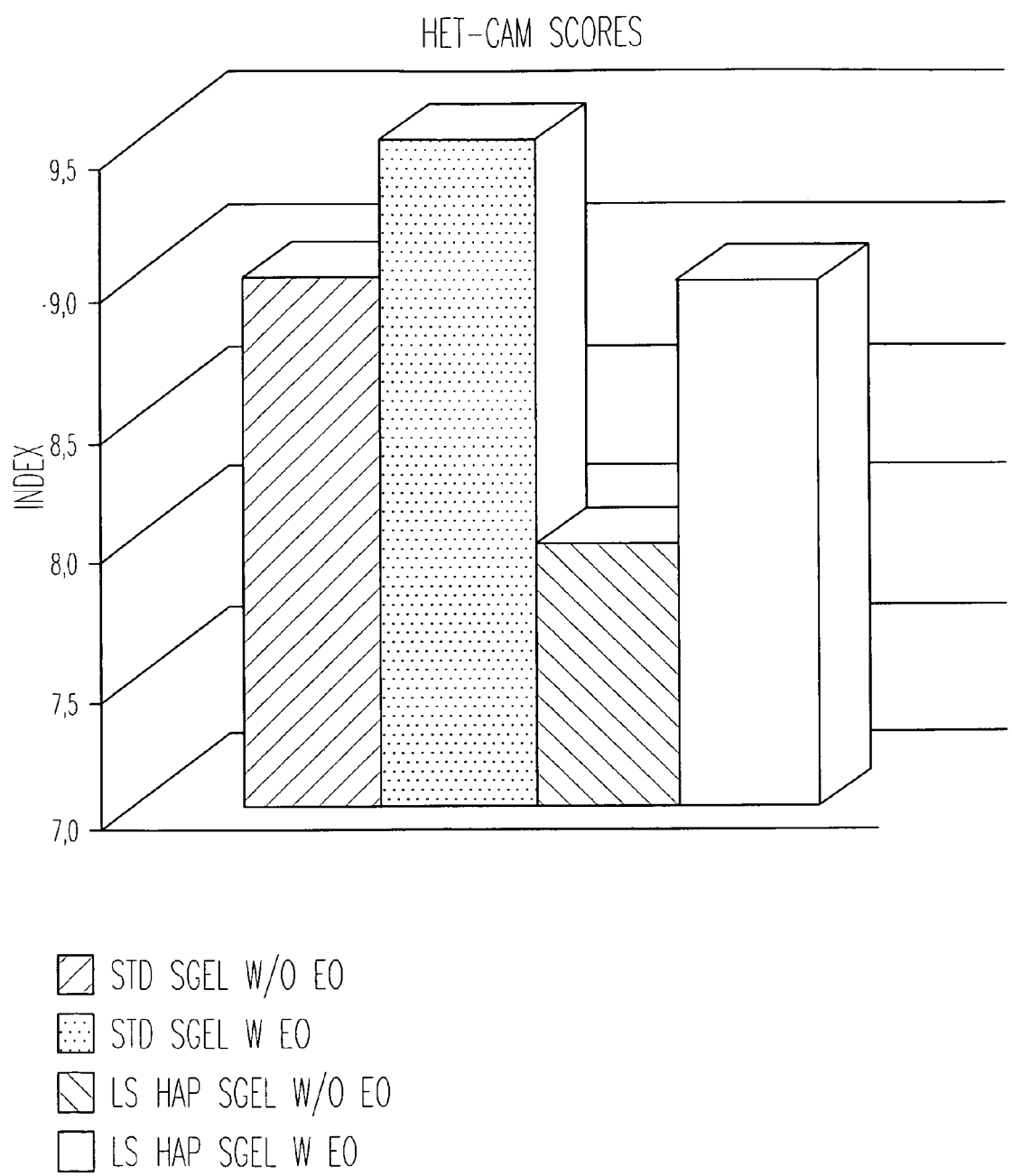
FIG. 2 is a bar graph depiction of the relative cytotoxicity as measured by the HET-CAM method of a bathing gel composition compared to a standard bathing gel composition.
Figure 3:
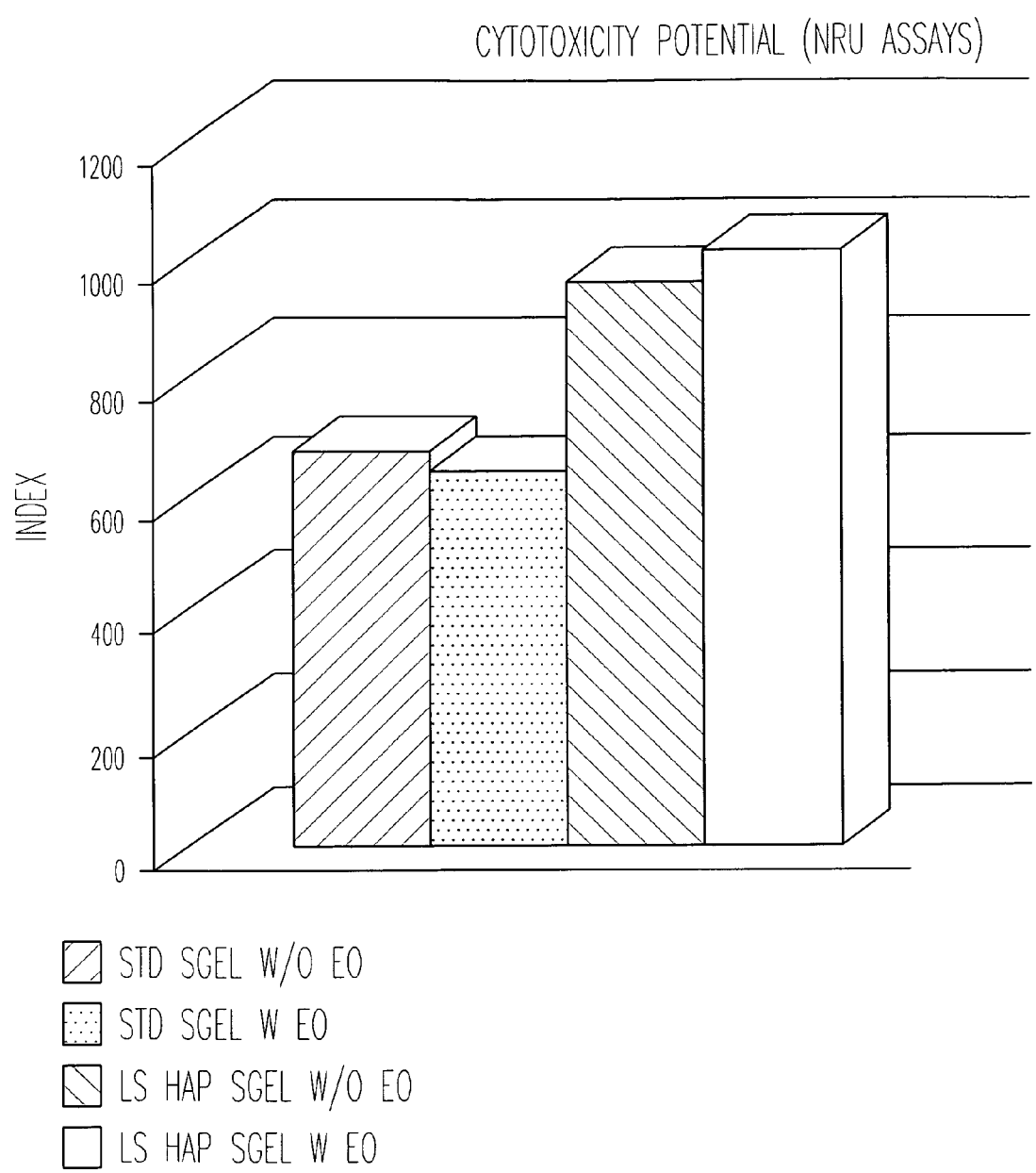
FIG. 3 is a bar graph depiction of the relative cytotoxicity as measured by the NRU method of a bathing gel composition compared to a standard bathing gel composition.

In various embodiments, the invention provides a wherein a skin mildness of the composition is at least as great as the skin mildness of a comparable composition lacking the long-chain alkyl hydroxyalkyl cellulose derivative and having a higher content of the anionic surfactant and, possibly, of fragrance oils as well. FIGS. 1-3 show results obtained with respect to a composition of the invention.

FIG. 1 shows a comparison of the cytotoxicity index, as measured by a Reconstituted Human Epithelial Culture (REC) assay, of a composition comprising (left to right) a control bathing gel without and with a fragrance oil (EO), as compared to a bathing gel of the invention without and with a fragrance oil (EO). The inventive bathing gel composition is comparable to the control but contains about 15-25% less fragrance oil. FIG. 2 shows a comparison of the Hen's Egg test on chorio-Allantoic Membrane (HET-CAM) scores of a composition comprising (left to right) a control bath gel without and with a fragrance oil (EO), as compared to a bath gel of the invention without and with a fragrance oil (EO). FIG. 3 shows a comparison of the cytotoxicity index, as measured by a Neutral Red Uptake (NRU) assay, of a composition comprising (left to right) a control bath gel without and with a fragrance oil (EO), as compared to a bath gel of the invention without and with a fragrance oil (EO). Each of these comparisons indicates that a composition of the invention performs as well as or better than a control composition in these assays, each of which are indicative for mucose mildness or good ocular tolerance.

In various embodiments, the invention provides a composition wherein foam generation upon lathering the composition on skin of a user is at least as great as foam generation of a comparable composition lacking the long-chain alkyl hydroxyalkyl cellulose derivative and having a higher content of the anionic surfactant when lathered on the skin of a user under comparable conditions.

Figure 4:
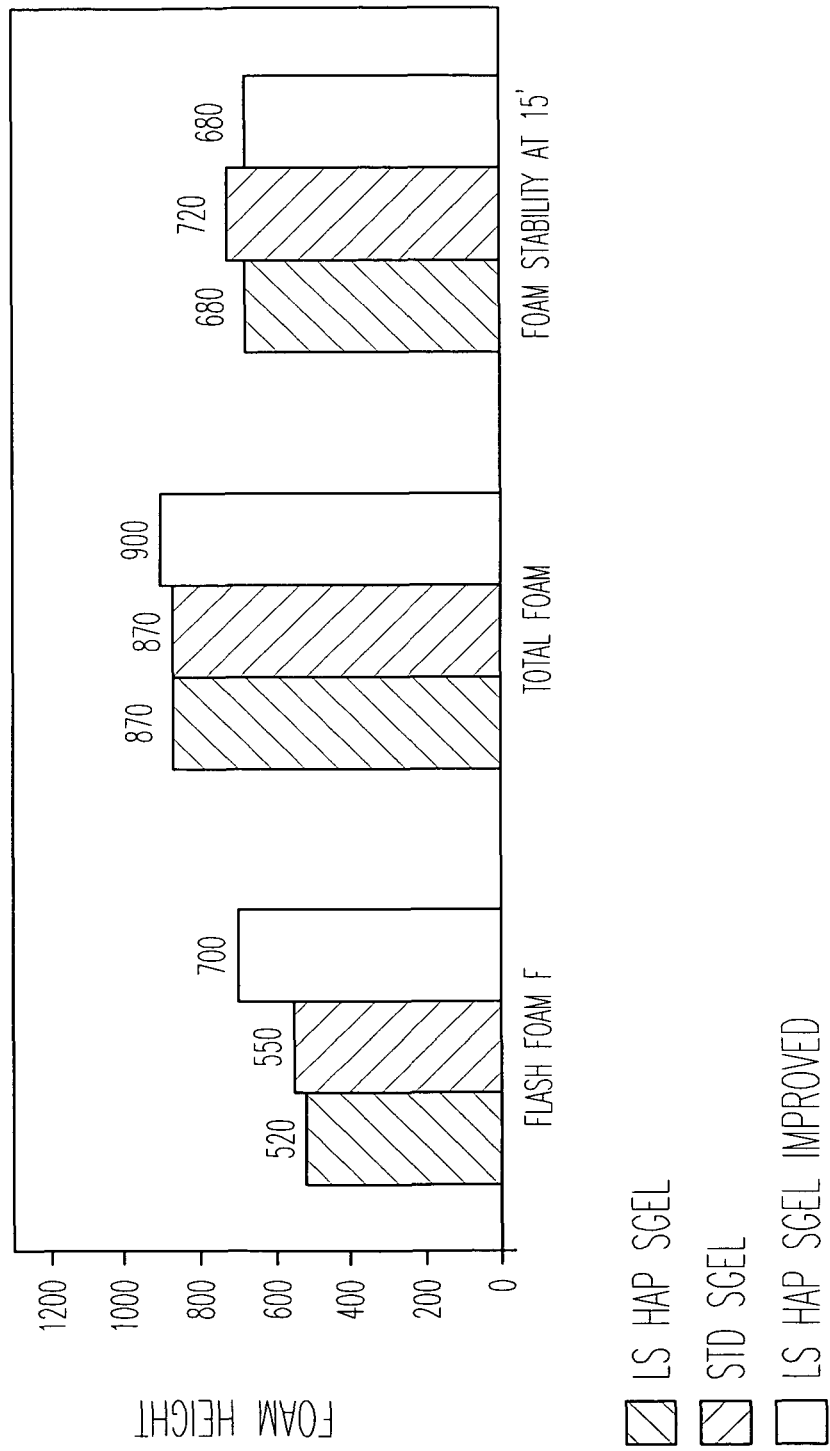
FIG. 4 is a bar graph depiction of foam performance of two inventive compositions versus a standard composition.

FIG. 4 shows graphic results of an evaluation of foam performance of two bathing gel compositions of the invention ("LS HAP SGel" and "LS HAP SGel Improved") versus a control bathing gel ("Std. SGel"), lacking the long-chain alkyl hydroxyalkyl cellulose derivative, and including a higher (>11.5%) total concentration of anionic surfactants. As is apparent, the performance of the two inventive bathing gel compositions is at least as good as the performance of the control gel in this evaluation. The evaluation was conducted using the C-TP-1494/1-Mod method, product concentration 1 g/L in tap water, sample volume 200 mL, T=25° C.±1° C., 10 total shakes, time measurements at 0 min (generation) and 15 min (decay).

Figure 5:
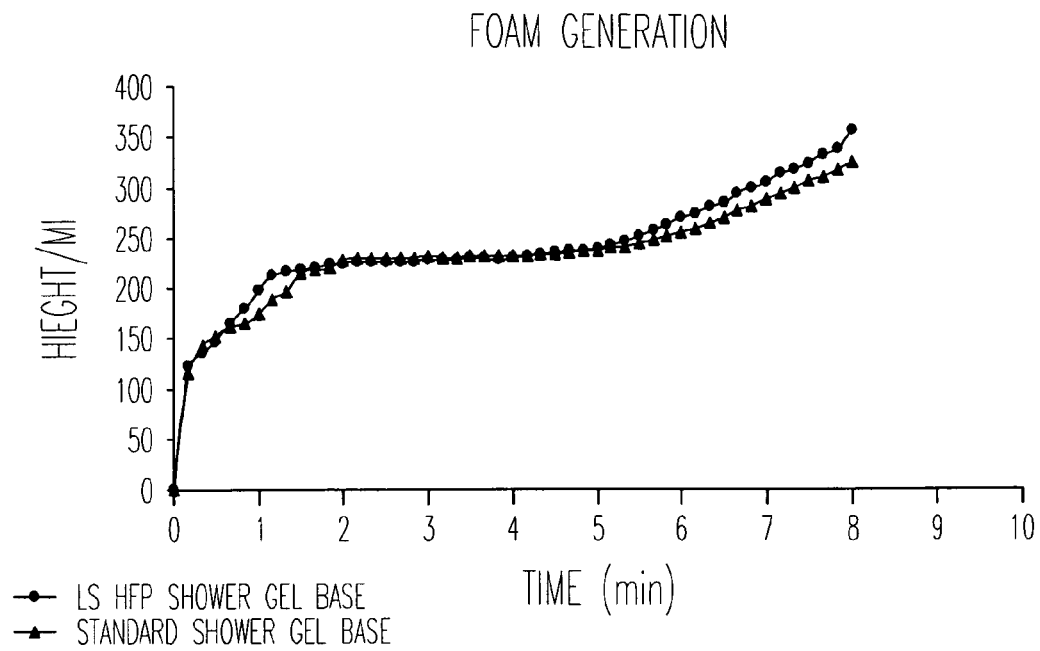
FIG. 5 is a graph of a time course of foam generation in an aqueous solution of a bathing gel composition of the invention versus a standard composition.
Figure 6:
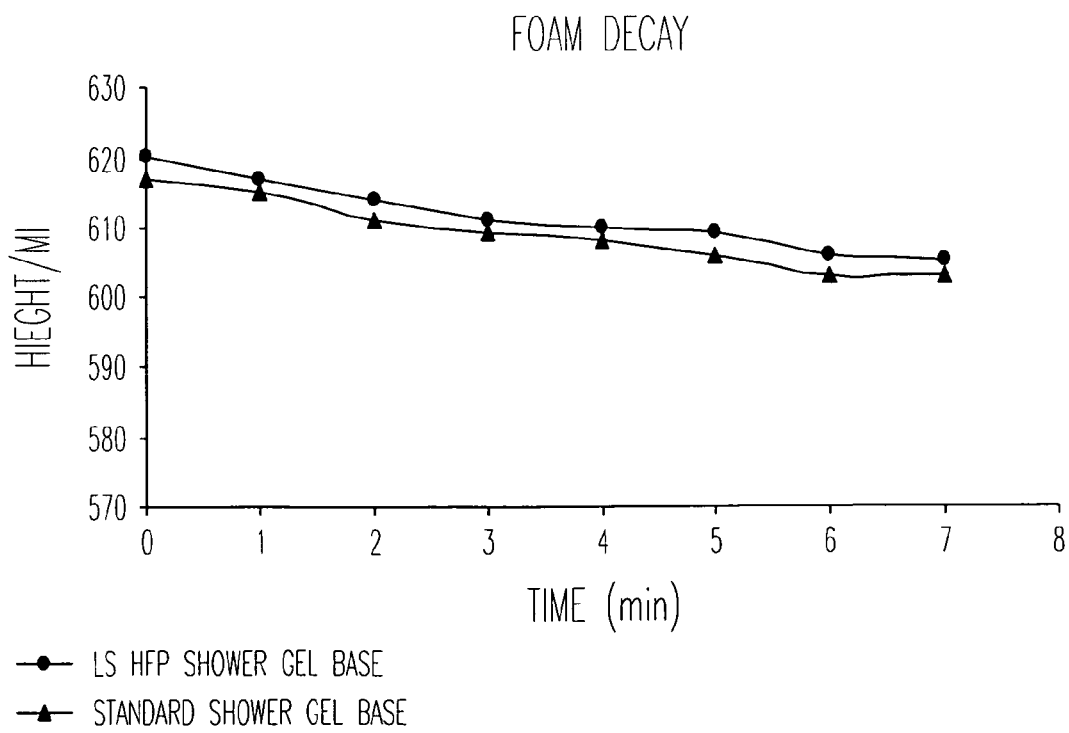
FIG. 6 is a graph of a time course of foam decay in an aqueous solution of a bathing gel composition of the invention versus a standard composition.

FIGS. 5 and 6 shows a graphic results obtained using a SITA Foam tester R-2000 of a comparison of foam generation and foam decay of a bathing gel composition of the invention ("LS-HFP shower gel base") versus a control composition ("standard shower gel base"). The test conditions were: product concentration 7 gm/L in deionized water, sample volume 250 ml, T=35° C.±1° C., rotor speed 950 rpm, stirring period 10 sec, total time 8 min (generation), 7 min (decay). As can be seen, an embodiment of the inventive bathing gel composition provides for foam generation and persistence at least as favorable as a standard control bathing gel composition.

Figure 7:
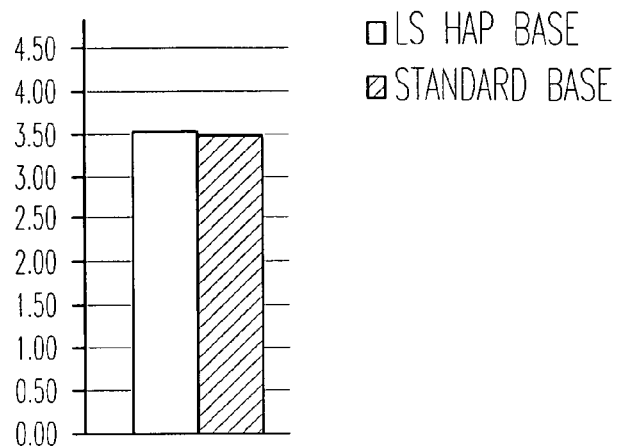
FIG. 7 shows a composite ranking of subjective cleansing appreciation by a group of 16 users.

In various embodiments, the invention provides a composition wherein a cleansing appreciation of a person using the composition is a least as great as a cleansing appreciation of a comparable composition lacking the long-chain alkyl hydroxyalkyl cellulose derivative and having a higher content of the anionic surfactant. FIG. 7 shows a subjective value for cleansing appreciation based on the results from a panel of 16 volunteers of an embodiment of an inventive composition versus a standard control bathing gel composition. As can be seen, there is no diminishment from the cleansing appreciation experienced by the users with the inventive composition with respect to the standard composition.

Figure 8:
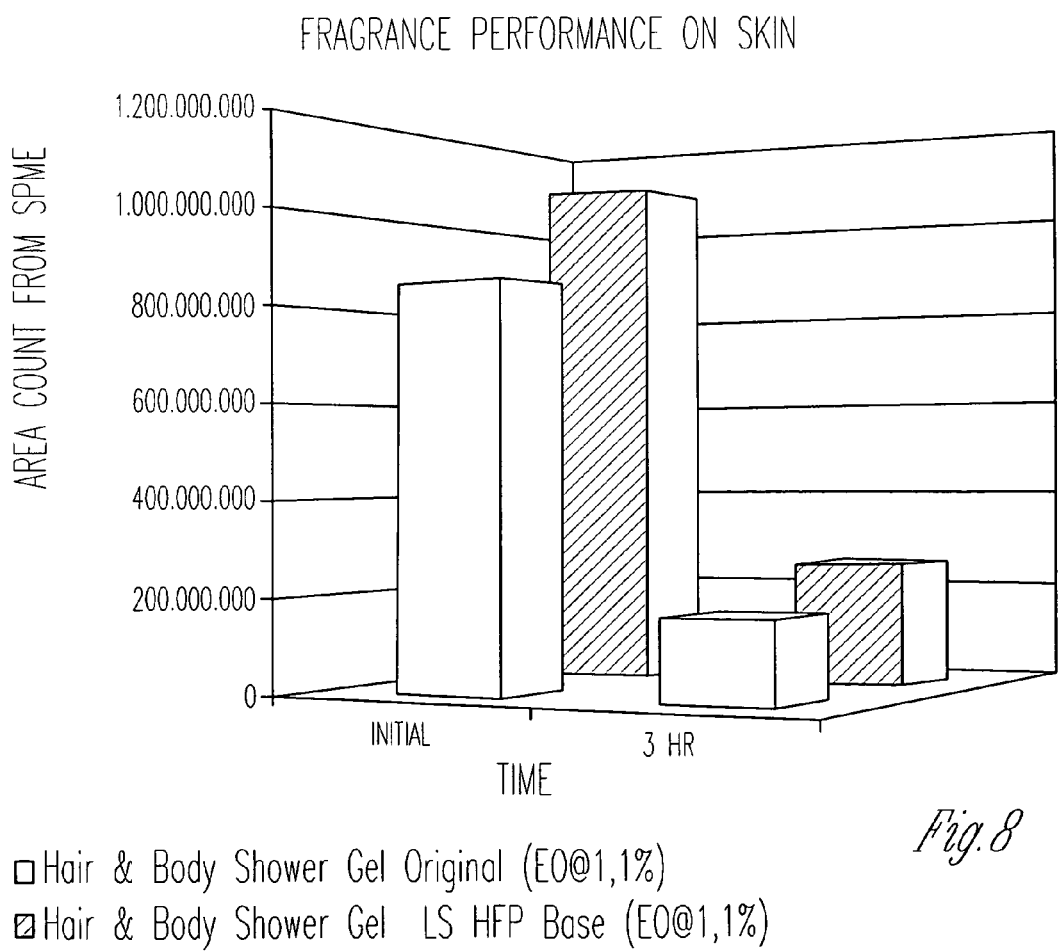
FIGS. 8 and 9 show a comparison of the fragrance performance on skin and in bottle headspace, respectively of a bathing gel composition of the invention versus a standard composition, with respect to a single fragrance oil.
Figure 9:
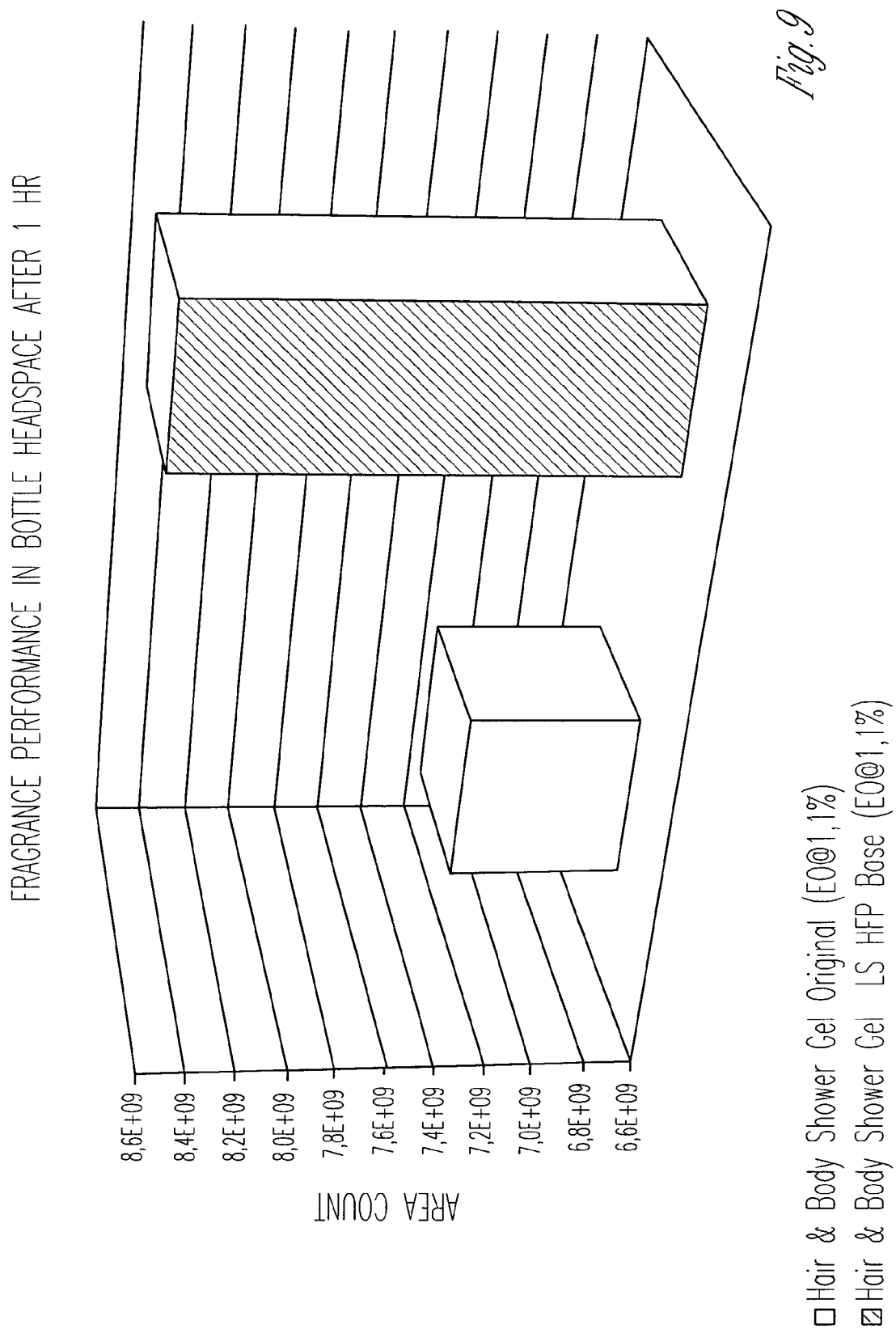

In various embodiments, the invention provides a composition comprising up to about 3% w/w of a fragrance oil, or up to about 2%, or up to about 1%, wherein a fragrance performance on skin, a fragrance performance in container headspace, or both, is no less than that of a comparable composition lacking the long-chain alkyl hydroxyalkyl cellulose derivative and having a higher content of the anionic surfactant. FIGS. 8 and 9 compare an embodiment of a composition of the invention versus a control bathing gel, at equal concentrations of fragrance oil (EO), about 1-1.3% w/w in the formation, for a single fragrance oil, on the skin and in bottle headspace. The fragrance performance was measured by solid phase microextraction (SPME) methodology. As can be seen, the "shower gel LS HFP base" (a composition of the invention), has superior fragrance performance on skin at 0 and 3 hr, and in bottle headspace, as compared to a standard bathing gel composition "shower gel original."

Figure 10:
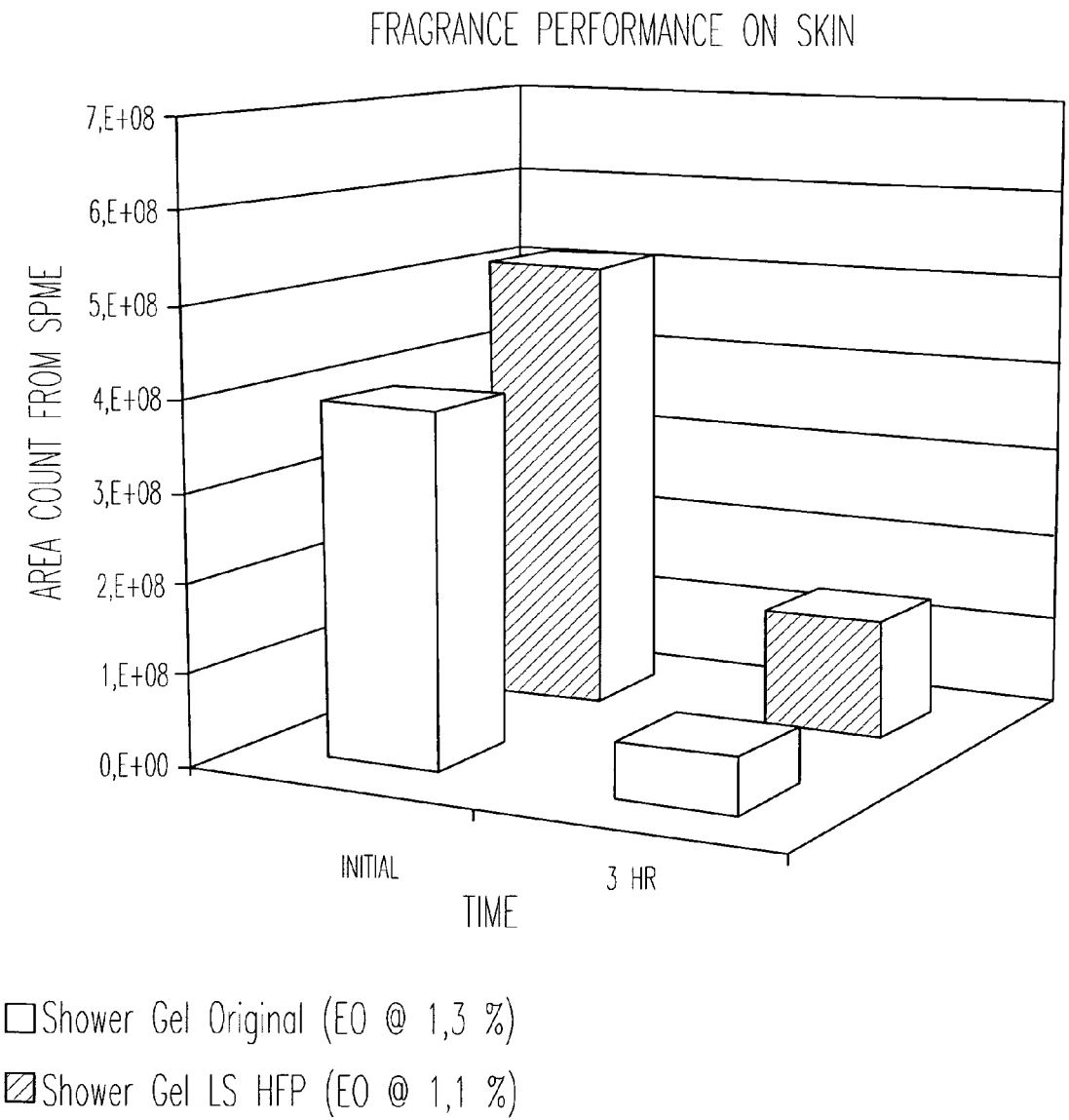
FIGS. 10 and 11 show a comparison of the fragrance performance on skin and in bottle headspace, respectively of a bathing gel composition of the invention versus a standard composition, averaged for six different fragrance oils.
Figure 11:
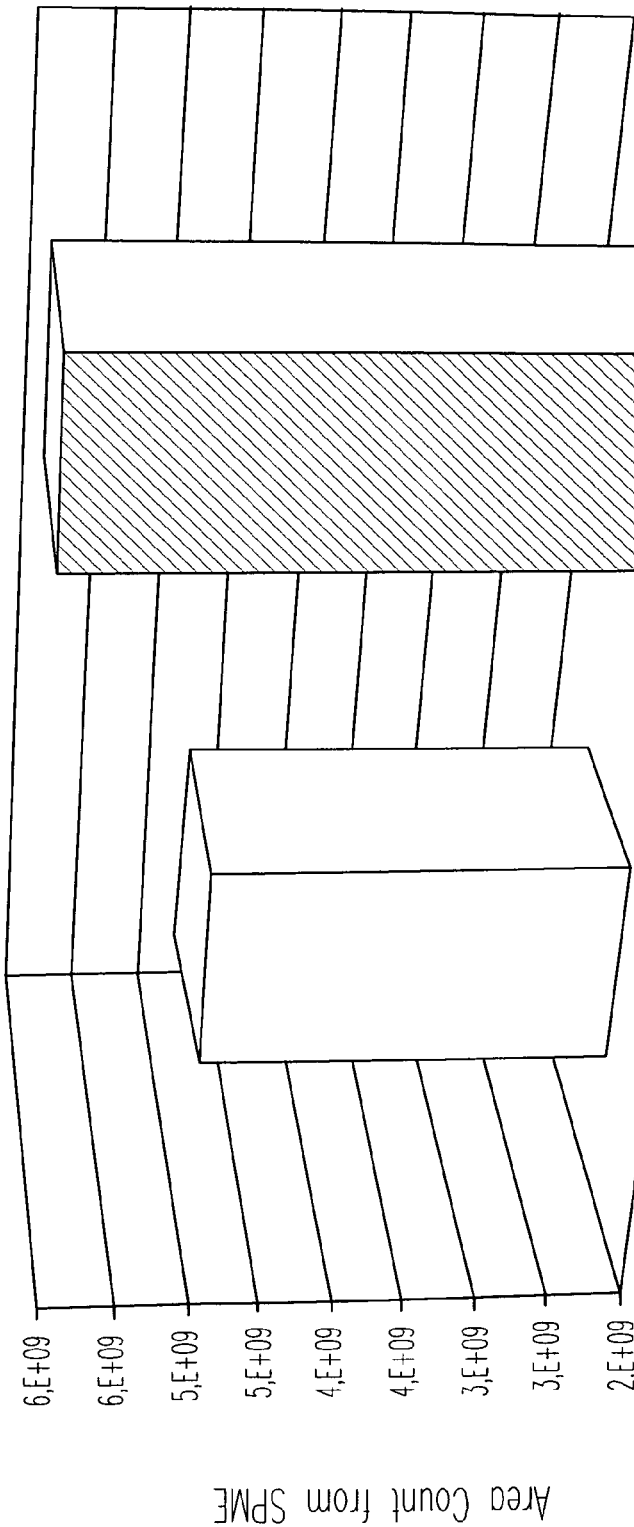

FIGS. 10 and 11 provide a similar comparison of fragrance oil on skin and in bottle headspace, except that the inventive composition has about a 15-25% lower concentration of fragrance oil, and the data represent the averages of results using the SPME method of six different fragrance oils. Again, the "shower gel LS HFP base" (a composition of the invention), has superior fragrance performance on skin at 0 and 3 hr, and in bottle headspace, as compared to a standard bathing gel composition "shower gel original."

In various embodiments, the invention provides a composition wherein an amount of the composition in water exhibits less toxicity to organisms in contact with the water than does an equivalent amount of a comparable composition lacking the long-chain alkyl hydroxyalkyl cellulose derivative and having a higher content of the anionic surfactant. A comparison of the relative aquatic toxicity profile of the long-chain alkyl hydroxyalkyl cellulose derivative compared to anionic alketh surfactant is shown in Table 3.

The terms used are defined as follows:

LC50 or EC50: Lethal or effect concentration 50=Concentration in water having 50% chance of causing adverse effects or death to aquatic life)

$SF_{acute}$: Safety Factor, determined according the number of trophic levels (fish, crustaceous, algae) studied (the largest, the best)

$TF_{acute}$: $L(E)C50/SF_{acute}$

NOEC: No observed effect concentration=The highest concentration for which the difference from the control group is not statistically significant in a long term study $SF_{chronic}$: Safety Factor, determined according the number of trophic levels (fish, crustaceous, algae) studied $TF_{chronic}$: $NOEC/SF_{chronic}$ In various embodiments, the invention provides a method of reducing a surfactant concentration in bath or shower wastewater, comprising use by a person for personal cleansing in the bath or shower of a quantity of the composition of the invention as a substitute for use of a comparable quantity of a comparable composition lacking the long-chain alkyl hydroxyalkyl cellulose derivative and having a higher content of the anionic surfactant.

In various embodiments, the invention provides a method of decreasing a surfactant load on a wastewater treatment facility, comprising use by a person for personal cleansing in the bath or shower of a quantity of the composition of the invention as a substitute for use of a comparable quantity of a comparable composition lacking the long-chain alkyl hydroxyalkyl cellulose derivative and having a higher content of the anionic surfactant.

Various embodiments of bathing gel compositions of the invention retain a spectrum of performance attributes that are no less than and in some cases substantially better than a standard composition bathing gel, such as viscosity, skin mildness, foam generation, user-perceived cleansing appreciation, and fragrance oil performance, but contain significantly less anionic surfactant content. As discussed above, the decrease in the anionic surfactant concentration, in conjunction with the retention of consumer-desired performance attributes at a comparable or better level, will result in use of a comparable amount of an inventive bathing gel by a consumer, that comparable amount containing a lesser absolute

TABLE 3

Acute and Chronic Aquatic Toxicity of Cetyl Hydroxyethyl Cellulose versus an Alketh Sulfate Surfactant

| | Acute toxicity (aquatic trophic levels) | | | Chronic toxicity (aquatic trophic levels) | | |
|---|---|---|---|---|---|---|
| | LC50 or EC50 | $SF_{acute}$ | $TF_{acute}$ | NOEC | $SF_{chronic}$ | $TF_{chronic}$ |
| C 12/15 A 1-3 EO sulfate | 4.1 | 1000 | 0.0041 | 0.1 | 10 | 0.01 |
| Cetyl Hydroxyethyl cellulose | 1000 | 10000 | 0.1 | 600 | 100 | 6 |

As is apparent, a reduction of several percent in the concentration of the anionic surfactant in conjunction with the addition of about 0.1-0.5% w/w to a bathing gel will result in a bathing gel that has less aquatic toxicity per unit weight or volume of the composition as packaged for sale and use by the consumer. The anionic surfactant exhibits a much greater degree of both acute and chronic aquatic toxicity than does cetyl hydroxyethyl cellulose, and diminishing the amount per volume of this material having a relatively high aquatic toxicity, and replacing it with a smaller amount of a much less aquatically toxic product, will serve to decrease the overall aquatic toxicity of a composition of the invention relative to a comparable control composition of bathing gel. The consumer-valued properties as listed above, being equal to or better than the properties of commercially available bathing gels, will enable the user to portion out an equivalent volume of the product when bathing, as there would be no incentive to use more to achieve a property such as foaming or cleansing appreciation beyond that which is achieved using the commercially available product.

In various embodiments, the invention provides a composition wherein a greater proportion of the composition is biodegraded in wastewater or in an aquatic ecosystem under comparable conditions than a biodegraded proportion of a comparable composition lacking the long-chain alkyl hydroxyalkyl cellulose derivative and having a higher content of the anionic surfactant.

quantity of surfactant. Accordingly, wastewater streams from bathing with an inventive composition bathing gel contain a lower concentration and a lower total load of surfactant compared to wastewater streams resulting from bathing with a standard bathing gel.

Wastewater streams are typically either fed into sewage disposal systems for primary and sometimes secondary treatment in a wastewater (sewage) treatment facility that releases its effluent into surface waters, or are disposed of in domestic septic tank systems that release their effluent into soil and groundwater. Accordingly, in various embodiments, the invention provides that reducing surfactant concentration in bathing wastewater or decreasing a surfactant load in a wastewater stream can provide an environmental benefit to an ecosystem into which the wastewater is disposed. Particularly where the effluent of the sewage treatment process or septic tank is present at a relatively high localized concentration in surface or ground water, the aggregate reduction in surfactant loading that results from use of an inventive composition for bathing can have a significant positive impact on ecosystem health. For example, discharge of treated wastewater having a lower concentration of relatively toxic anionic surfactants by a sewage treatment facility into wetlands would result in a decrease in the toxicity to aquatic organisms brought about by the discharge. The health of wetlands is known to be vital to the maintenance of undamaged ecosystems because so many environmentally sensitive species depend on clean water in a wetlands habitat. This environmental benefit can translate to improved human health as well when a human population consumes the products of a wetland environment, such as various plant crops, fish, waterfowl, and the like.

In various embodiments, the invention provides a method of improving environmental sustainability comprising replacing use of a shower gel or bath gel personal cleansing product comprising a quantity of one or more anionic surfactant substances with a shower gel or bath gel personal cleansing product comprising a lesser quantity of one or more anionic surfactant substances and further comprising at least about 0.1% of a long-chain alkyl hydroxyalkyl cellulose derivative, preferably cetyl hydroxyethylcellulose. By reducing the wastewater loading of the relatively toxic components of bathing gel compositions, and thus improving the health of aquatic and groundwater habitats into which treated (or untreated) sewage is disposed, a lesser environmental impact is achieved without a diminishment of the quality of life of persons using an environmentally friendly bathing gel of the present invention.

In various embodiments, the inventive composition or method can be any one of any of the combinations and/or sub-combinations of the above-listed embodiments.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference to the same extent as if each individual publication was specifically and individually indicated to be incorporated by reference.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A composition for use as a shower gel or bath gel personal cleansing product by human users, consisting essentially of:
    (a) no more than about 11.5% w/w of an anionic surfactant;
    (b) no more than about 3% w/w of a zwitterionic surfactant;
    (c) no less than about 0.1% w/w of a long-chain alkyl hydroxyalkyl cellulose derivative; and
    (d) water,
and optionally further comprising up to no more than about 2% w/w of a non-ionic surfactant, or up to no more than about 3% w/w of a fragrance oil, or both.

2. The composition of claim 1 that is in physical state a viscous liquid or a gel at room temperature.

3. The composition of claim 1 comprising no more than about 10% w/w of the anionic surfactant.

4. The composition of claim 1 wherein the anionic surfactant comprises an alketh sulfate, an alkyl sarcosinate salt, or any combination thereof.

5. The composition of claim 1 wherein the anionic surfactant comprises sodium laureth sulfate, sodium lauroyl sarcosate, or sodium cocoyl sarcosate, or any combination thereof.

6. The composition of claim 1 comprising no more than about 2.4% w/w of the zwitterionic surfactant.

7. The composition of claim 1 wherein the zwitterionic surfactant comprises a fatty amidoalkylbetaine.

8. The composition of claim 7 wherein the fatty amidoalkylbetaine comprises cocamidopropylbetaine.

9. The composition of claim 1 comprising no more than about 0.5% w/w of a non-ionic surfactant.

10. The composition of claim 1 wherein the a non-ionic surfactant comprises a fatty mono-glucoside or a fatty polyglucoside, or any mixture thereof.

11. The composition of claim 1 wherein the fatty glucoside is coco-glucoside.

12. The composition of claim 1 comprising no less than about 0.3% w/w of the long-chain alkyl hydroxyalkyl cellulose derivative.

13. The composition of claim 1 wherein the long-chain alkyl hydroxyalkyl cellulose derivative comprises cetyl hydroxyethyl cellulose.

14. The composition of claim 1, comprising:
    (a) no more than about 8.0% w/w of an anionic surfactant;
    (b) no more than about 2.4% w/w of a zwitterionic surfactant;
    (c) no less than about 0.3% w/w of a long-chain alkyl hydroxyalkyl cellulose derivative; and
    (d) water;
    optionally further comprising up to about 3% w/w of a fragrance oil;
    wherein the composition is in physical form a viscous liquid or a gel at room temperature.

15. The composition of claim 14, further comprising no more than about 0.3% w/w of a non-ionic surfactant, preferably a fatty alkyl glucoside, more preferably coco-glucoside.

16. The composition of claim 1 wherein a viscosity of the composition is at least as great as a viscosity of a comparable composition lacking the long-chain alkyl hydroxyalkyl cellulose derivative and having a higher content of the anionic surfactant.

17. The composition of claim 1 wherein a skin mildness of the composition is at least as great as the skin mildness of a comparable composition lacking the long-chain alkyl hydroxyalkyl cellulose derivative and having a higher content of the anionic surfactant.

18. The composition of claim 1 wherein foam generation is at least as great as foam generation of a comparable composition lacking the long-chain alkyl hydroxyalkyl cellulose derivative and having a higher content of the anionic surfactant when lathered on the skin of a user under comparable conditions.

19. The composition of claim 1 wherein a cleansing appreciation of a person using the composition is a least as great as a cleansing appreciation of a comparable composition lacking the long-chain alkyl hydroxyalkyl cellulose derivative and having a higher content of the anionic surfactant.

20. The composition of claim 1 comprising up to about 3% w/w of a fragrance oil, or up to about 2%, or up to about 1%, wherein fragrance performance on skin, fragrance performance in container headspace, or both, is no less than the fragrance performance on skin or in container headspace of a comparable composition lacking the long-chain alkyl hydroxyalkyl cellulose derivative and having a higher content of the anionic surfactant.

21. The composition of claim 20 wherein the fragrance oil is present at a lower concentration than a fragrance oil component of a comparable composition lacking the long-chain alkyl hydroxyalkyl cellulose derivative and having a higher content of the anionic surfactant and wherein a fragrance performance on skin, a fragrance performance in container headspace, or both, is no less than that of the comparable composition lacking the long-chain alkyl hydroxyalkyl cellulose derivative and having a higher content of the anionic surfactant.

22. The composition of claim 1 wherein an amount of the composition in water exhibits less toxicity to organisms in contact with the water than does an equivalent amount of a comparable composition lacking the long-chain alkyl hydroxyalkyl cellulose derivative and having a higher content of the anionic surfactant.

23. The composition of claim 1 wherein a greater proportion of the composition is biodegraded in wastewater or in an aquatic ecosystem than a biodegraded proportion of a comparable composition lacking the long-chain alkyl hydroxyalkyl cellulose derivative and having a higher content of the anionic surfactant under comparable conditions.

24. Use of the composition of claim 1 for preparation of a personal cleansing product.

25. A method of reducing a surfactant concentration in bath or shower wastewater, comprising use by a person for personal cleansing in the bath or shower of a quantity of the composition of claim 1 as a substitute for use of a comparable quantity of a comparable composition lacking the long-chain alkyl hydroxyalkyl cellulose derivative and having a higher content of the anionic surfactant.

26. A method of decreasing a surfactant load on a wastewater treatment facility, comprising use by a person for personal cleansing in the bath or shower of a quantity of the composition of claim 1 as a substitute for use of a comparable quantity of a comparable composition lacking the long-chain alkyl hydroxyalkyl cellulose derivative and having a higher content of the anionic surfactant.

27. The method of claim 25 wherein the reducing provides an environmental benefit to an ecosystem into which the wastewater is disposed.

28. The method of claim 26 wherein the decreasing provides an environmental benefit to an ecosystem into which the wastewater is disposed.

29. The method of claim 25 wherein a purer effluent stream of treated wastewater from a facility treating the wastewater is achieved thereby.

30. The method of claim 26 wherein a purer effluent stream of treated wastewater from a facility treating the wastewater is achieved thereby.

31. A method of reducing toxicity of wastewater to organisms in contact with the wastewater caused by use of a quantity of a shower gel or bath gel personal cleansing product, comprising use by a person for personal cleansing in the bath or shower of the quantity of a composition of claim 1 as a replacement for use of an equivalent quantity of a comparable composition lacking the long-chain alkyl hydroxyalkyl cellulose derivative and having a higher content of the anionic surfactant.

32. A method of improving biodegradability of wastewater resulting from use of a quantity of a shower gel or bath gel personal cleansing product, comprising use by a person for personal cleansing in the bath or shower of the quantity of a composition of claim 1 as a replacement for use of an equivalent quantity of a comparable composition lacking the long-chain alkyl hydroxyalkyl cellulose derivative and having a higher content of the anionic surfactant.

33. A method of reducing the amount of fragrance oil discharge by wastewater into an ecosystem resulting from use of a quantity of a shower gel or bath gel personal cleansing product, comprising use by a person for personal cleansing in the bath or shower of the quantity of a composition of claim 1 as a replacement for use of an equivalent quantity of a comparable composition lacking the long-chain alkyl hydroxyalkyl cellulose derivative and having a higher content of the anionic surfactant, wherein the composition of claim 1 comprises a lower concentration of the fragrance oil than does the comparable composition, wherein fragrance performance on skin, fragrance performance in container headspace, or both, of the composition is no less than the fragrance performance on skin or in container headspace of the comparable composition.

34. A method of improving environmental sustainability resulting from use of a shower gel or bath gel personal cleansing product, comprising use by a person for personal cleansing in the bath or shower of the equivalent quantity of a composition of claim 1 as a replacement for use of an equivalent quantity of a comparable composition lacking the long-chain alkyl hydroxyalkyl cellulose derivative and having a higher content of the anionic surfactant.

* * * * *